United States Patent [19]

Donald

[11] 4,309,997
[45] * Jan. 12, 1982

[54] CONTRACEPTIVE AND/OR ANTIVENEREAL DISEASE TAMPON

[76] Inventor: Jack W. Donald, Suite C, 10780 Pebble Hills, El Paso, Tex. 79935

[ * ] Notice: The portion of the term of this patent subsequent to Feb. 5, 1997, has been disclaimed.

[21] Appl. No.: 132,843

[22] Filed: Mar. 24, 1980

Related U.S. Application Data

[63] Continuation-in-part of Ser. No. 76,164, Sep. 17, 1978, which is a continuation of Ser. No. 888,578, Jun. 6, 1978, Pat. No. 4,186,742.

[51] Int. Cl.³ ............................................. A61F 13/20
[52] U.S. Cl. .................................................... 128/270
[58] Field of Search ......................... 128/263, 270, 285

[56] References Cited

U.S. PATENT DOCUMENTS

| | | |
|---|---|---|
| 467,599 | 1/1892 | Abundi et al. . |
| 639,864 | 12/1899 | Von Raitz . |
| 969,640 | 9/1910 | Langstaff . |
| 2,687,729 | 8/1954 | Slavin . |
| 3,067,745 | 12/1962 | Burgeni et al. . |
| 3,128,762 | 4/1964 | Young . |
| 3,429,312 | 2/1969 | Stump ................................. 128/263 |
| 3,594,468 | 7/1971 | Saurino et al. . |
| 3,639,561 | 2/1972 | Gordon et al. ...................... 128/270 |
| 3,639,562 | 2/1972 | Gordon et al. . |
| 3,691,271 | 9/1972 | Charle et al. ....................... 128/285 |
| 3,762,414 | 10/1973 | Burnhill ............................. 128/285 |
| 3,794,029 | 2/1974 | Dulle . |
| 3,814,809 | 6/1974 | Gordon ................................ 424/19 |
| 3,875,300 | 4/1975 | Homm et al. . |
| 3,918,452 | 11/1975 | Cornfeld . |
| 3,995,633 | 12/1976 | Gougeon . |
| 4,066,075 | 1/1978 | Hughes . |
| 4,108,180 | 8/1978 | Moehrle ............................. 128/285 |

FOREIGN PATENT DOCUMENTS 2011102 3/1970 Fed. Rep. of Germany .

Primary Examiner—C. Fred Rosenbaum
Attorney, Agent, or Firm—Bacon & Thomas

[57] ABSTRACT

A new concept of pregnancy and disease prevention is provided by a medicated tampon in the form of a soft, porous foam ball of substantially spherical configuration, which is easily insertable into the vagina to cover the cervical area and which is impregnated with a contraceptive for control of pregnancy, and/or with a safe spectrum of antibiotics for control of venereal disease. The tampon may be inserted before intercourse to remain in place during intercourse.

5 Claims, 3 Drawing Figures

CONTRACEPTIVE AND/OR ANTIVENEREAL DISEASE TAMPON

CO-PENDING APPLICATIONS

This application is a continuation-in-part of my co-pending application Ser. No. 76,164 filed Sept. 17, 1978 which application in turn is a continuation of my application Ser. No. 888,578 now U.S. Pat. No. 4,186,742 filed on June 6, 1978.

FIELD OF INVENTION

This invention relates to the field of control of conception and/or to venereal disease control.

DESCRIPTION OF THE PRIOR ART

Prior art methods are known for preventing conception by utilization of vaginal suppositories, foams or creams along with tampons containing contraceptive compositions. The prior art means of preventing conception are often inconvenient to use or have physiological or psychological drawbacks.

U.S. Pat. No. 3,594,468 shows a sphermacidal and germicidal composition which can be used in tablets, capsules, suppositories, powders, jellies, liquids, sprays and on fabrics.

U.S. Pat. No. 3,639,562 shows a vaginal suppository or impregnated tampon to be inserted after intercourse.

U.S. Pat. No. 3,691,271 shows a sanitary napkin with microcapsules filled with a bactericidal and fungicidal deodorant.

U.S. Pat. No. 3,918,452 shows an impregnated tampon or vaginal sponge, for insertion with a mechanical device, and which is treated with a contraceptive drug that is microencapsulated so that there is a sustained release of contraceptive composition before, during and/or after coitus.

DESCRIPTION OF THE PRESENT INVENTION

The present invention is intended to eliminate the difficulties and objections to prior art tampons. The worldwide problems of over population necessitate a more effective and generally acceptable means of control of conception. Venereal disease control is a continuing problem requiring constant search for more effective methods. The treated tampon of the present invention is a step forward toward effective control of either or both problems. My prior application Ser. No. 888,578 (U.S. Pat. No. 4,186,742) disclosed and claimed a tampon containing control agents for both purposes but obviously such tampon could be treated with only one control agent where only one type of control is desired.

The tampon of the invention comprises a soft, porous, foam shape of substantially spherical configuration in the uncompressed state and of a size and compressibility to fit snugly within the vagina of the human female to cover the cervical area while permitting intercourse to take place. The spherical configuration of the tampon permits easy insertion into the vagina without the necessity of orientation and there is no need for a special applicator. The tampon is medicated for contraception by impregnation with a solution containing a safe and effective contraceptive control agent preferably which is not absorbable through the membranes into the system of the user. Alternatively, it may be medicated for venereal disease control with a safe and effective venereal disease control agent, also preferably one which is not absorbable. Such agents are individually known to the art and are commercially available as over the counter products but have never been used in the manner of the present invention.

The material of the tampon is preferably a soft, light weight, physiologically inert foam material of polyurethane, polyether, polyester, or the like which is of a very fine porosity and which when compressed will return to substantially its original shape. Such foam materials are known to the art. The tampon surface should be relatively smooth and substantially free of fibers. The tampon may be made by a molding process and a string may be attached by embedding one end in the foam during the molding process. The string is optional and is for the purpose of facilitating removal of the tampon after use. Alternatively, the tampon may be cut from a block of foam by use of a hot wire or other cutting means which will result in a smooth surface free of fibers which might cause irritation to sensitive membranes.

The contraceptive agent of the tampon is preferably one which contains Nonoxynol as the active spermacidal ingredient. This is a well known sphermacide which is safe and effective for vaginal use. It has the formula:

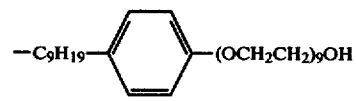

However, it will be understood that other sphermacidal agents as may be found to be safe and effective may be used.

The venereal disease control agent, where this is the function desired, is preferably a safe spectrum of antibiotics known to be effective against venereal disease causative agents. The control agent is suitably an antibiotic selected from the group consisting of salts of bacitracin, neomycin, polymyxin B or a mixture of such substances. It is preferred to use a mixture because of the wide spectrum of germicidal activity obtained. It will be understood that other germicides as may be found safe and effective for venereal disease control may be used.

The contraceptive and/or venereal disease control agent is conveniently placed in an aqueous solution or emulsion containing glycerin or the like for moistening and lubricating functions and the solution is then used to impregnate the spherical porous, foam tampon. Preferably the solution is buffered to a pH of about 4.5, the natural pH of the vagina, before use. The amounts of active ingredients used in the tampon are those which are found to be effective for the contraceptive and/or venereal disease control functions.

In one embodiment of the invention, the tampon is a spherical ball of approximately 4.1 centimeters (1⅝ inches) in diameter of a smooth and very fine porosity, soft, light weight polyurethane or polyester foam, made by a molding process with the end of a 3" string, of the type commonly used in sanitary tampons, embedded into the ball during the molding process for easy removal of the tampon after use. In another embodiment, the tampon may be simply cut to the desired spherical size and shape by means of a hot cutting wire which smooths off objectionable fibers as it cuts. The preferred foams are inert materials and are non-reactive to the human body. The tampon is sterilized, and dipped into a solution of glycerin and water that contains, for example, the spermicide Nonoxynol in an amount of approximately 10% by weight, and is buffered to pH 4.5.

Alternatively, or additionally, the solution with which the tampon is dipped may contain, for example, the the following antibiotics per ounce of solution: zinc Bacitracin 12,000 units, Neomycin Sulphate 85 mg. and Polymyxin B Sulphate 250,000 units.

The invention will be further understood by reference to the drawings in which.

The ball may be inserted into the vagina with the finger, before sexual intercourse and should be left at least 2 hours after intercourse. No insertion device is necessary. The foam ball is conveniently packaged individually in a moisture proof package such as cellophane, foil or similar packaging.

Figure 1:
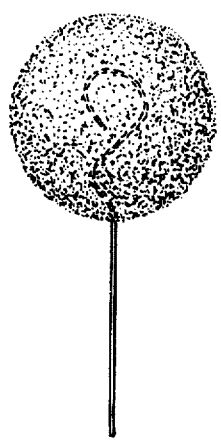
FIG. 1 is a view of the soft foam tampon of the invention in its uncompressed form prior to insertion in the vagina.
Figure 2:
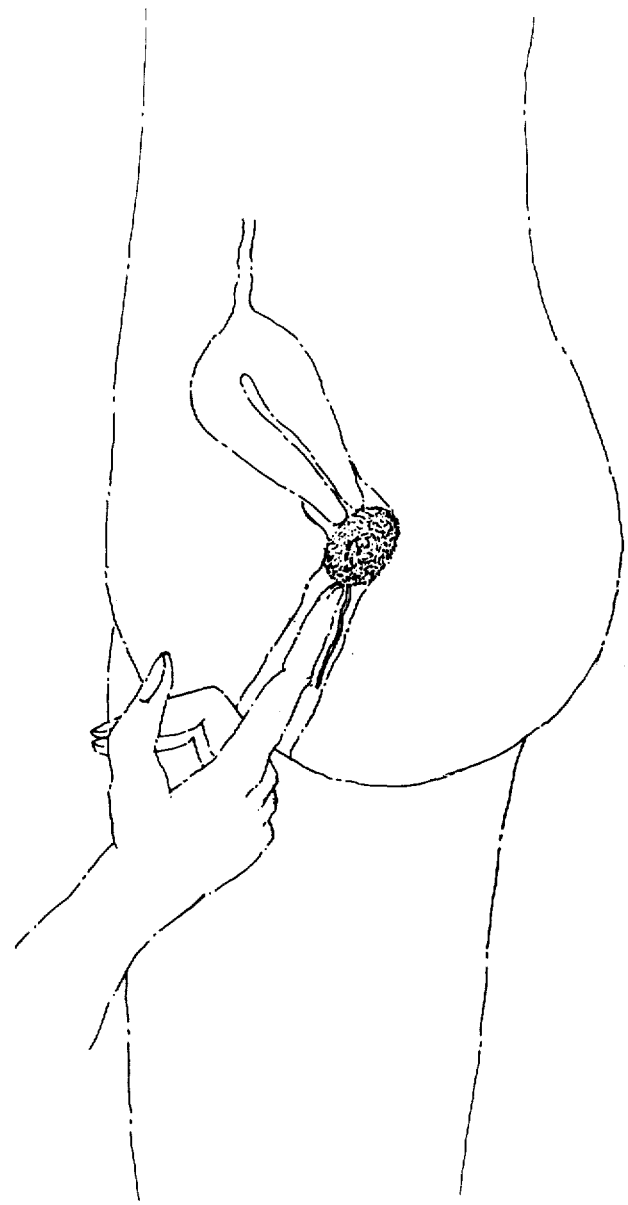
FIG. 2 is a diagrammatic illustration showing the placement of the tampon in the vagina to cover the cervical area.
Figure 3:
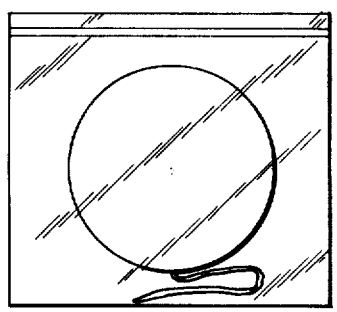
FIG. 3 is a side view of a transparent package containing one of the tampons of the invention.

Since the device is spherical in configuration it is not necessary that it be oriented prior to or after insertion. As seen in FIG. 2, it will inherently assume the configuration of the vaginal area during use.

I claim:

1. A moist medicated vaginal tampon for contraceptive and venereal disease control comprising a soft, porous foam ball of substantially spherical configuration in the uncompressed state and of a size and compressibility to fit snugly within the vagina of a human female to cover the cervical area while permitting intercourse to take place, said spherical configuration permitting easy insertion without the necessity of orientation, said porous foam ball being impregnated with a solution containing a germicidal agent of the type and in an amount effective to control venereal disease and a contraceptively effective amount of a contraceptive agent.

2. The vaginal tampon as defined in claim 1, wherein the tampon is of soft polyurethane foam of very fine porosity.

3. The vaginal tampon as defined in claim 1, wherein the foam ball has a diameter of about 4.1 centimeters.

4. The vaginal tampon as defined in claim 1, which is contained singly in a moisture proof package.

5. A method for contraceptive and venereal disease control comprises the step of applying to the vaginal cavity of a mammalian female the vaginal tampon as defined in claim 1, precoitus and retaining it in the vaginal cavity during sexual intercourse.

* * * * *